US00PP14627P39

(12) United States Plant Patent
Byrne et al.

(10) Patent No.: US PP14,627 P3
(45) Date of Patent: Mar. 23, 2004

(54) PEACH TREE NAMED 'TEXKING'

(50) Latin Name: *Prunus persica*
Varietal Denomination: TexKing

(75) Inventors: David Byrne, Bryan, TX (US); Terry Bacon, Bakersfield, CA (US)

(73) Assignee: The Texas A&M University System, College Station, TX (US)

( * ) Notice: Subject to any disclaimer, the term of this patent is extended or adjusted under 35 U.S.C. 154(b) by 37 days.

(21) Appl. No.: 10/114,819

(22) Filed: Apr. 2, 2002

(65) Prior Publication Data

US 2003/0188352 P1 Oct. 2, 2003

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Fulbright & Jaworski LLP

(57) ABSTRACT

A new and distinct variety of *Prunus persica* is provided. The new peach tree variety produces an attractively colored, yellow fleshed, clingstone peach that matures early in the season (7–10 days after Flordaking) under the ecological conditions prevailing in the medium chill zone of south central Texas and is adapted in the medium chill region. The variety requires approximately 450 chilling units of dormancy.

5 Drawing Sheets

Variety denomination: Variety of *Prunus persica,* denominated as 'TexKing'.

BACKGROUND OF THE INVENTION

The present invention relates to a new, novel and distinct variety of *Prunus persica* (L.) Batsch, which has the denominated varietally as 'TexKing'. The 'TexKing' Peach Tree produces a high quality, yellow fleshed, firm clingstone peach which matures early in the season. Another unique aspect of the 'TexKing' is that requires approximately 450 chilling units of dormancy.

BRIEF SUMMARY OF THE INVENTION

The 'TexKing' peach is characterized as to novelty and is otherwise noteworthy by producing a high quality, firm, and attractive fruit which ripens in the early season following the variety 'Flordaking' (not patented) (Andrews et al. 1979, *HortScience* 14:81–82). In this regard, the present variety of peach tree bears fruit that are ripe for commercial harvesting in early to middle May, when the variety is grown in central Texas, which is about 7 to 9 days after the fruit of 'Flordaking' (not patented). Growing the variety in the ecological conditions of central San Joaquin Valley (Fowler, Calif.), the commercial harvesting is early June. Additionally, 'TexKing' exhibits the potential to be commercialized in medium chill regions.

ORIGIN OF THE VARIETY

The present peach tree was the result of an ongoing Stone Fruit Breeding Program of Texas A&M University, College Station, Tex. To this end, both controlled and hybrid crosses are made each year in order to produce seedling populations from which improved progenies are evaluated and selected.

'TexKing' (*Prunus persica* (L.) Batsch originated in the Stone Fruit Breeding Program at the Department of Horticultural Sciences, Texas A&M University, College Station, Tex. The seed parent was 'Goldprince', a nonpatented variety released in 1989 by the USDA Stone Fruit Breeding Program located in Byron, Ga. (Okie, 1993, *HortScience* 28:231). This peach was crossed with the selection TX3290-2 which was a large fruited, early ripening, medium chill selection from a cross between the selection Y7-97× 'Hamlet'. 'Hamlet' is a non-patented peach released from a North Carolina breeding program (Clayton et al., 1977, *Fruit Var. J.* 31:34–35). Y7-97 was selected at the Yoakum Plant Disease Experiment Station from a population derived from a cross made at Rutgers University on a tree of a New Jersey peach selection (CITY32-423) with pollen from a selection (C9-42) from the University of Florida.

In 1992, the cross was made, embryos were rescued, and the seedlings were planted in a high-density fruiting nursery at College Station in 1993. In 1994, 'TexKing' was selected under the selection name of 'TX2B6' for having exceptional characteristics, including early maturity, large fruit size, good productivity, yellow ground color, round shape, high red overcolor, and excellent firmness. It was propagated asexually by budding and has been evaluated in Texas, California, and southern Spain.

ASEXUAL REPRODUCTION

In May 1997, the new variety 'TexKing' was bud grafted onto virus-free 'Nemaguard' (The Brooks and Olmo Register of Fruit and Nut Varieties, 3$^{rd}$ Ed., American Society of Horticultural Science Press, Alexandria, Va., 1997) peach rootstock. 'TexKing' was propagated at the experimental orchards of Texas A&M University near the city of College Station (Brazos County, Tex.) and near the city of Yoakum (Dewitt County, Tex.) in the south central region of Texas and at experimental orchards near the city of Fowler (Fresno County, Calif.) in the central portion of the San Joaquin Valley of California. Fruit from the resulting propagation has been evaluated from 1994 to 2001 in College Station, from 1997 to 2001 in Yoakum, and from 1999 to 2001 in Fowler. This evaluation clearly demonstrated that the repropagated trees are true to the characteristics of the original seedling in all observable aspects.

BRIEF DESCRIPTION OF THE DRAWINGS

For a more complete understanding of the present invention, reference is now made to the following descriptions taken in conjunction with the accompanying drawing, in which.

DETAILED BOTANICAL DESCRIPTION

Figure 1:
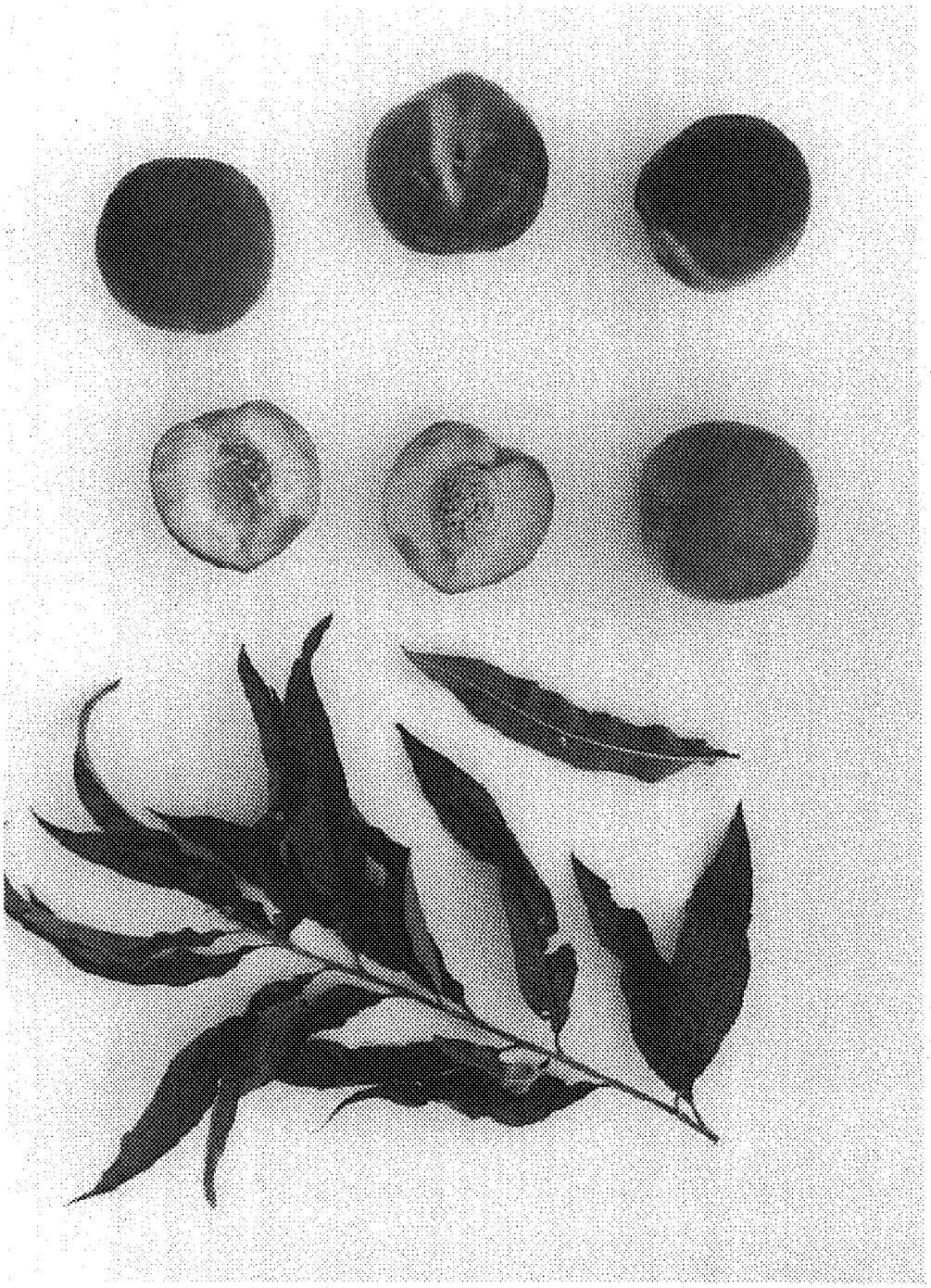
FIG. 1. is a color photograph of a characteristic twig bearing typical leaves; several leaves showing both the dorsal and ventral coloration, and several mature fruit showing their external coloration sufficiently matured for harvesting and shipment. Additionally, one fruit of the subject variety is dissected in the axial or suture plane to illustrate the flesh and stone characteristics thereof. This fruit was harvested from experimental plots in Fowler, Fresno County, Calif.
Figure 2:
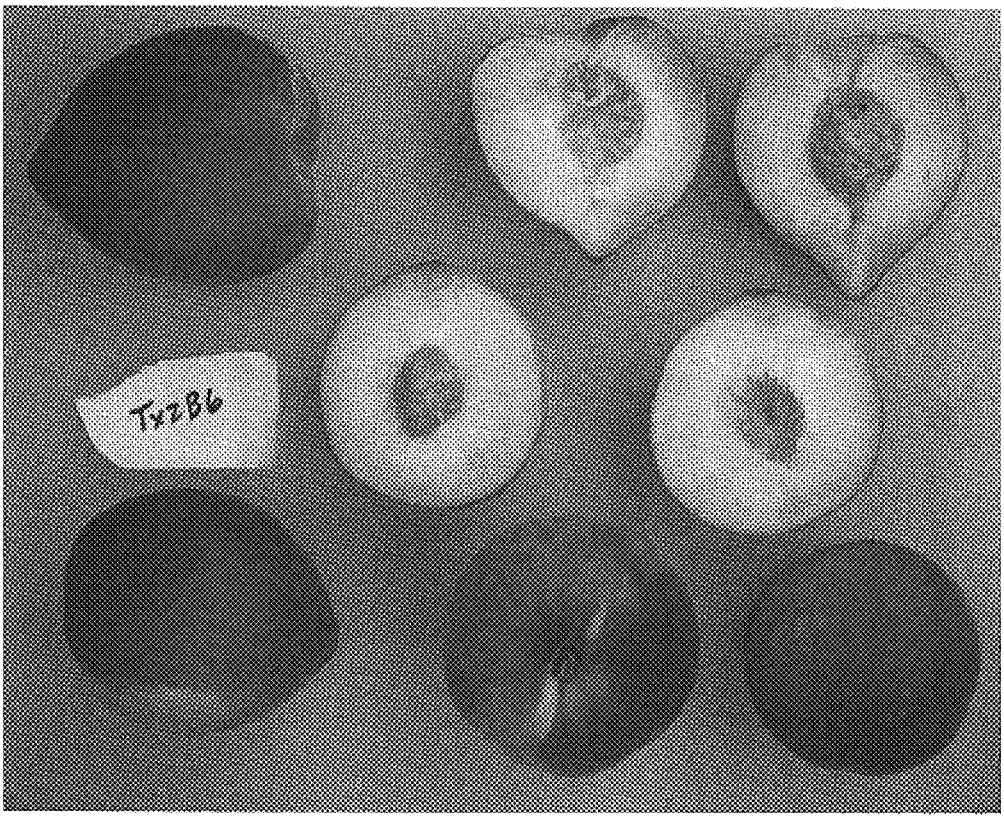
FIG. 2. is a color photograph of external and internal views of fruit 'TexKing' produced in the experimental orchards in south central Texas to show the typical color and shape observed when grown in a medium chill zone.
Figure 3:
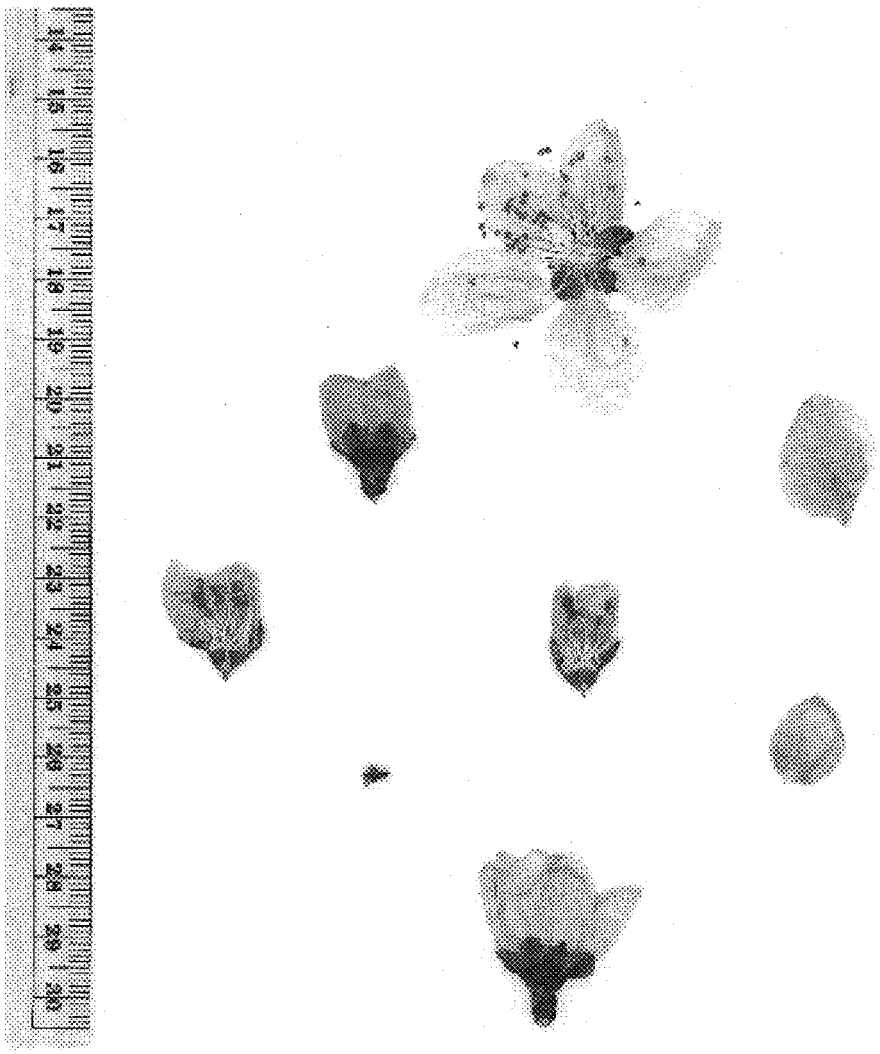
FIG. 3. is a color photograph of flowers of 'TexKing' propagated in an experimental orchard in south central Texas.
Figure 4:
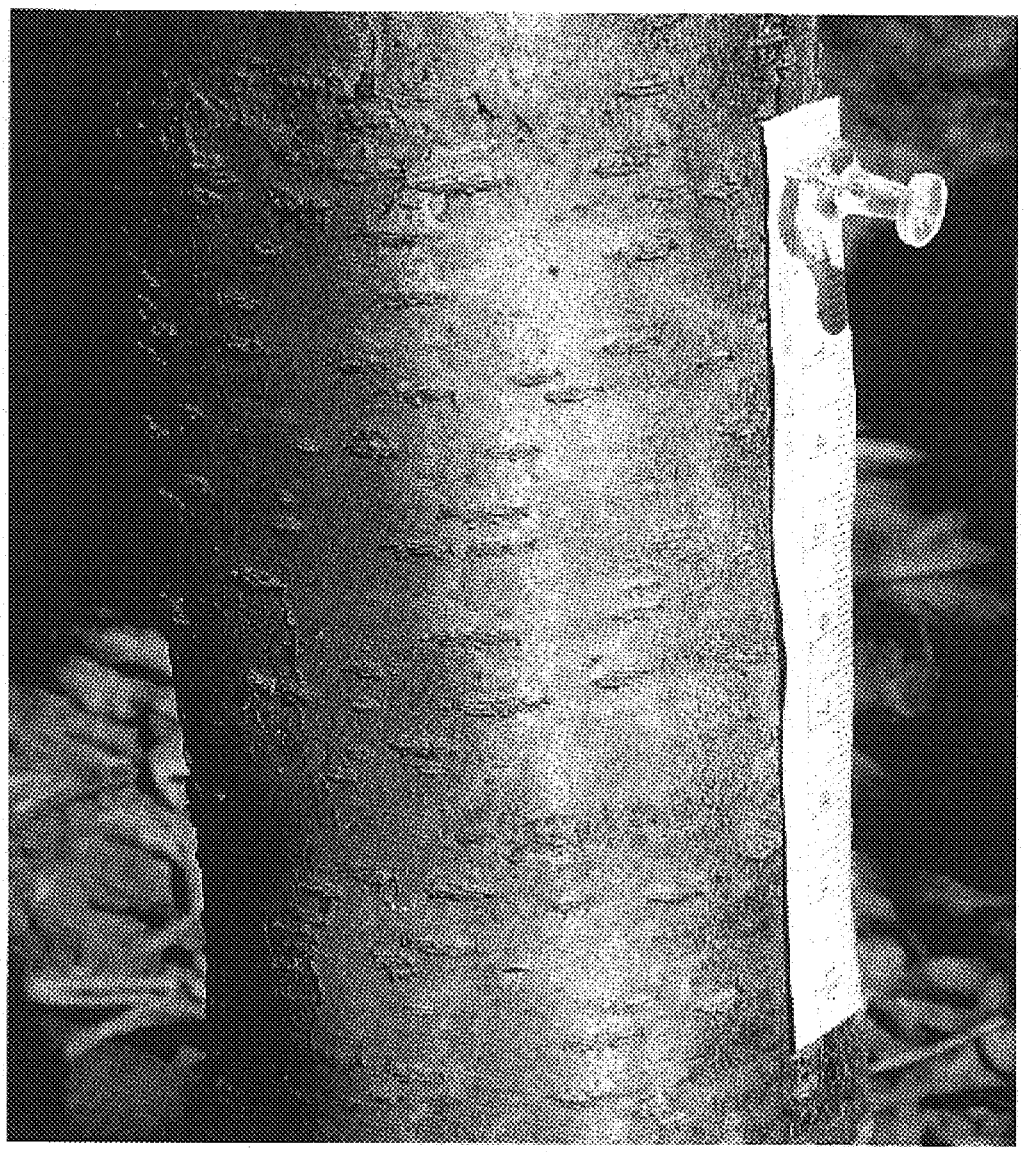
FIG. 4. shows the bark of 'TexKing' propagated in an experimental orchard in south central Texas.
Figure 5:
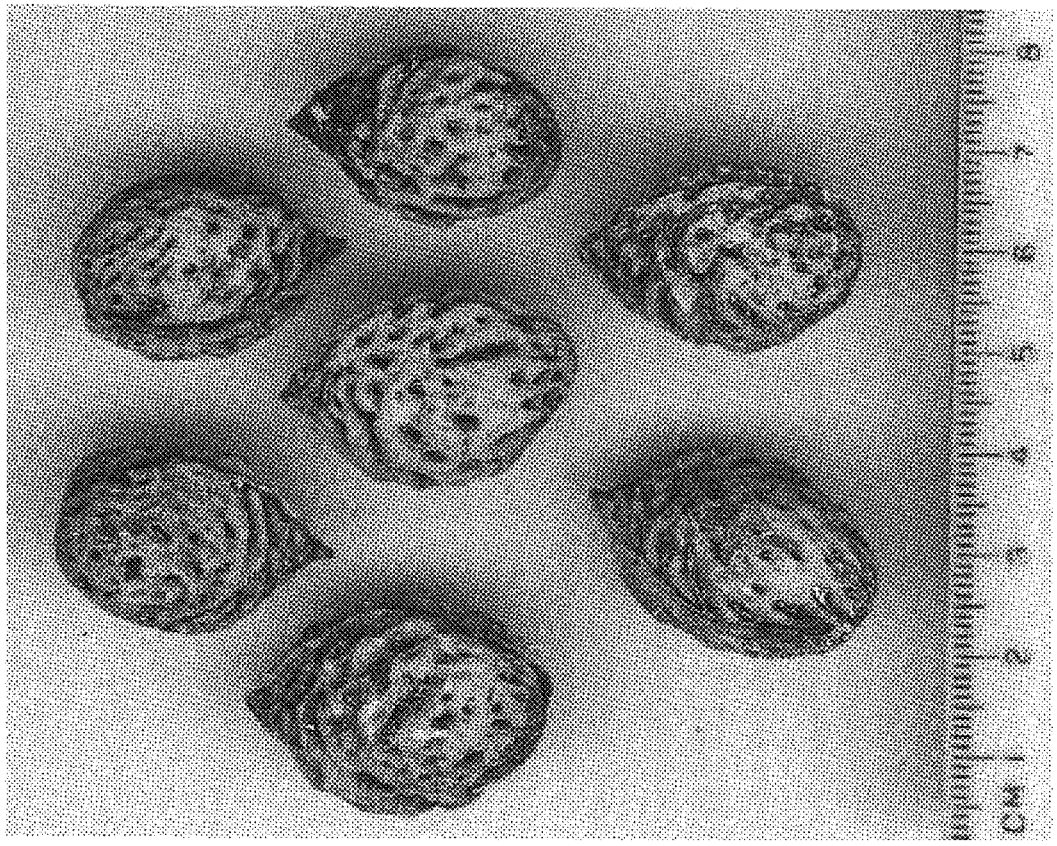
FIG. 5. shows pits (endocarp) from the fruit of 'TexKing' produced in an experimental orchard south central Texas.

Referring more specifically to the pomological details of this new and distinct variety of peach tree, the following has been observed under the ecological conditions prevailing at the experimental orchards near the town of Fowler, Fresno county, Calif. and of Texas A&M University at sites in College Station, Brazos county and near Yoakum, DeWitt county, Tex. The color and size designations are from samples collected in the experimental orchards of Texas A&M University unless otherwise noted. All major color code designations are by reference to The R.H.S. Colour Chart (Third Edition) provided by The Royal Horticultural Society of Great Britain and descriptors are from the New Jersey Agricultural Experiment Station Bulletin 728 entitled, 'Standards for Classifying Peach Characters' by M. A. Blake and L. J. Edgerton published in 1946. Colors are approximate, as color depends on horticultural practices such as, for example, light level and fertilization rate.

Tree:

*Size.*—Average to above average as compared to other common peach cultivars ripening in the early season of maturity.

*Productivity.*—Very productive and self-fertile. Fruit set must be thinned to avoid limb breakage and to obtain the desired size.

*Form.*—The 'TexKing' peach has been trained in central leader configuration in California and an open center configuration in Texas. Training and pruning methods of trees controls branch size and crotch angles. Thus the natural growth habit of the tree is not seen since poorly angled (narrow) or positioned branches are removed. When trained as an open center, it displays a semi-upright growth habit.

*Height and width.*—Height of 3.0 meters and a width of 2.0 meters at end of third year of growth.

*Current season growth.*—The current season growth for the new variety ranged from 70 mm to 120 mm.

*Regularity of bearing.*—Regular and considered hardy under typical central San Joaquin Valley, Calif. and south central Texas conditions.

Trunk:

*Thickness.*—Ranged from 8.7 to 11.0 cm in diameter when measured at a distance of approximately 30 cm above the soil level, at the end of the third growing season.

*Bark texture.*—Considered moderately smooth.

*Lenticels.*—Numerous flat, oval lenticels present. The lenticels range in size from approximately 5.0 to 9.0 millimeters in width and from 1 to 2 millimeters in height. The color of the raised part of the lenticels was approximately RHS Greyed Orange Group 166D.

*Bark coloration.*—Variable, but it is generally considered to be a grey-brown (RHS Grey Brown Group 166A) with silver colored (RHS Black Group 202D) cracks oriented vertically.

Branches:

*Size.*—Considered medium for the variety.

*Thickness.*—The average diameter of the branches of these trees ranged from 4.3 to 5.5 cm.

*Surface texture.*—Relatively smooth with moderate furrowing and a medium density of lenticels attaining the size of the lenticels found on the trunk and older scaffolds.

*Current season shoots.*—Surface texture — Substantially glabrous.

*Internode length.*—Approximately 2.0 to 2.1 cm.

*Color of mature branches.*—One year old branches were predominantly RHS Greyed Orange Group color of 200D and two-year old branches were medium brown (RHS Greyed Orange Group 165A).

*Current seasons shoots.*—Color — The youngest tissue is light green, (RHS Yellow Green Group 144B) and the oldest tissue is a medium brown (RHS Grey Brown Group 199A).

Leaves:

*Size.*—Considered moderately large for the species. Leaf measurements have been taken from vigorous upright current season growth approximately at mid-shoot.

*Leaf length.*—Approximately 170 to 190 millimeters.

*Leaf width.*—Approximately 31 to 35 millimeters.

*Leaf form.*—Lanceolate.

*Leaf tip form.*—Sharply acute. The tip often appears flexed downwards and slightly twisted laterally.

*Leaf color.*—Approximately RHS Yellow Green Group 147A. Young leaves were the green designated with RHS Green Group 137B color chip.

*Lower surface.*—Approximately RHS Yellow Green Group 147B.

*Mid-vein.*—Light yellow green (RHS Yellow Green Group 157C).

*Leaf margins.*—Form — Considered crenate. Uniformity — Considered generally uniform.

*Leaf petioles.*—Size — Considered medium to medium long. Length — Approximately 7 to 10 mm. Thickness — Approximately 1.5 to 2 mm. Color — Pale green (RHS Yellow Green Group 146D).

*Leaf glands.*—Size — Small, approximately 1–2 mm in length and width. Number — 0 to 2. Type — Globose. Color — RHS Brown Group 200B.

*Leaf stipules.*—Size — Medium-long for the variety. Length — Approximately 12 to 15 mm. Form — Lanceolate in form and a crenate margin. Color — Green (RHS Yellow Green Group 146C) when young. The stipules are considered to be early deciduous.

Flowers:

*Flower buds.*—General — The floral buds are considered to be medium to medium large in size, conic in form, and slightly appressed relative to the bearing shoot. Bud length 5.5 mm. Bud width 2.8 mm. Bud colors, 166A and 165A of Greyed Orange Group. Color — The bud scales are grey-brown (RHS Greyed Orange Group 177D). The buds are considered hardy under typical central San Joaquin Valley, Calif. and south central Texas climatic conditions.

*Blooming type.*—Considered early in relation to other peach cultivars commonly growing in the central San Joaquin Valley. Date of full bloom in central San Joaquin Valley was about Feb. 11, 2000, and date of full bloom in central Texas was about February 14.

*Flower type.*—Showy.

*Flower size.*—Flower diameter at full bloom is approximately 39 millimeters.

*Bloom quantity.*—Considered abundant.

*Flower bud frequency.*—Normally 1 to 2 appear per node.

*Petal size.*—Considered medium to medium large for the species. Length — Approximately 20 millimeters. Width — Approximately 15 to 20 millimeters.

*Petal form.*—Broadly ovate.

*Petal count.*—Nearly always 5.

*Petal color.*—Light to medium pink (RHS Red Purple Group 62C).

*Petal margins.*—Generally considered variable, from nearly smooth, to undulate and ruffled.

*Petal apex.*—The petal apices appear slightly domed.

*Flower pedicel.*—Length — Considered medium-short, and having an average length of approximately 2 to 3 millimeters. Thickness — Considered average, approximately 1 to 2 millimeters. Color — Green (RHS Green Group 143C).

*Calyx.*—Surface Texture — Generally glabrous. Color — A reddish purple (approximately RHS Greyed-Red Group 59 B).

*Sepals.*—Surface Texture — The surface has a short, fine, wooly texture. Size — Sepal length 11.5 mm, sepal width 6 mm and ovate in form. Color — A dull red (approximately RHS Greyed-Red Group 183 B).

*Anthers.*—General — Anther length 1.0 mm. Anther width 0.5 mm. Color — Yellow (approximately RHS Yellow Group 8B) with a orange-red (RHS Orange-Red Group 34B) edge.

*Pollen production.*—Pollen is yellow (RHS Yellow-orange Group 19B) and abundant.

*Filaments.*—Size — Average 15 millimeters. The filaments generally protrude slightly greater than the pistil (average length of 12 millimeters). Color — Young filaments are white (RHS White Group 155C) and change to red purple (RHS Red Purple Group 60C) with age.

*Pistil.*—Relatively short in length, and slightly shorter, relative to the general anther height, overall. Length — Approximately 12 millimeters, including the ovary. Color — Considered yellow green (approximately RHS Green Yellow Group 1C).

*Surface texture.*—The variety has a long, slender pubescent pistil.

Fruit:

*Maturity when described.*—The present variety of fruit is described, as it would be found in its firm ripe condition at full commercial maturity. Under the ecological conditions prevailing in the San Joaquin Valley of central California, the date of the first picking was May 28, 2000, and the date of the last picking was Jun. 10, 2000. In the orchards near south central Texas, the commercial harvest began about the Jun. 7, 2001 and ended about Jun. 17, 2001.

*Size.*—General — Medium to medium large for the season and considered relatively uniform. Average Fruit Weight — 132 to 170 grams when thinned to about one fruit per 20 centimeters of fruiting wood, and varies with tree age, soil type, climatic conditions, and cultural practices. Average Cheek Diameter — Approximately 65 to 78 millimeters when properly thinned to about one fruit per 20 centimeters of fruiting wood. Average Suture Diameter — Approximately 68 to 74 millimeters. Average Axial Diameter — Approximately 74 to 77 millimeters.

*Fruit form.*—Round to ovate in its lateral aspect. The fruit is generally uniform in symmetry with when viewed from the apical aspect. It will have a rounder shape when grown under high chill and cool spring conditions, as exemplified in the San Joaquin Valley in central California, as compared to the more ovate shape developed under lower chill and warmer spring conditions as experienced in the south central Texas evaluation sites.

*Fruit suture.*—General — The suture appears as a thin line that extends from the base to the apex. No apparent callusing or stitching exists along the suture line. The suture may protrude slightly. Color — The suture normally is the same colors as the underlying blush, the red blush color ranges from a RHS Red Group 46B to a 53A with many degrees of shading and blending occurring between these colorations.

*Ventral surface.*—Form — Considered uniform.

*Stem cavity.*—Narrowly oval with a length of 18–20 mm, a width of 7–8 mm, and a depth of 7–10 mm.

*Fruit base.*—Considered truncate in form, and uniform.

*Fruit apex.*—More prominent in a lower chill, warmer spring climate. In this characteristic, it is similar to the variety 'Flordaking'.

*Fruit skin.*—General — Considered medium to average in thickness. Surface Texture — The variety has very light, short pubescence. Skin Acidity — Considered neutral. Tenacious to Flesh — Yes at commercial maturity. Tendency to Crack — No cracking has been observed. Skin Color — Variable, with approximately 55% to 80% of the fruit surface covered with an attractive red blush. The red blush color ranges from a RHS Red Group of 46B to a 53A with many degrees of shading and blending occurring between these colorations. Blush Color — The red blush color ranges from a RHS Red Group of 46B to a 53A with many degrees of shading and blending occurring between these colorations. Skin Ground Color — generally present in variable percentages covering approximately 20% to 45% of the fruit's surface. The skin ground is yellow ranging within the RHS Yellow Orange Group From 15C to 18B.

*Flesh color.*—Considered variable from a yellow/orange and ranges between RHS Yellow Orange Group 14C to 17C chip color.

*Flesh texture.*—Generally considered firm and fine at commercial maturity. As the fruit as it approaches a ripe state, softening occurs first on the apical tip.

*Ripening.*—Generally ripens evenly.

*Flavor.*—Considered sweet and a rich, slightly acidic flavor. It has a brix of approximately 10 degrees.

*Aroma.*—Pleasant and reasonably abundant.

*Eating.*—Considered very good to excellent, particularly for an early ripening variety.

Stone:

*Attachment.*—Clingstone at commercial maturity.

*Stone size.*—General — Considered medium relative to the ratio of stone to fruit size. Length — Approximately 31.5 millimeters. Width — Approximately 20.6 millimeters. Thickness — Approximately 18.0 millimeters.

*Base angle.*—The base angle of the stone is variable, but most frequently is considered medium (70–79 degrees).

*Hilum.*—Oval with a length of 4–5 mm and a width of 2–3 mm.

*Apex.*—Raised and has an acute tip.

*Stone shape.*—Considered variable. The stone normally is equal, although occasionally may appear unequal. Its form is elliptical to ovate.

*Stone surface.*—Surface Texture — Generally considered medium in roughness and exhibits substantial pitting laterally. Grooves are formed by chains of pits particularly towards the apex of the stone.

*Dorsal edge.*—Broad and deep lines and a medium ridge.

*Stone color.*—The color of the dry stone is brown approximated by RHS Grey Brown Group 199D with the pits being the color RHS Brown Group 200 D.

*Tendency to split.*—Splitting has not been observed.

*Kernel.*—The kernel fills the inner cavity of the endocarp upon harvest but shrivels when dried. The dried kernel measures approximately 0.75–1.25 mm in thickness, 13.5–14.25 mm in length, and 6.5–8.0 mm in width. The predominant colors of the dried kernels are the RHS Greyed Orange Group colors of 164A, 165A and 165B.

*Use.*—The subject variety, 'TexKing', is considered to be a peach tree of early season maturity, which produces fruit that are firm, attractively colored, and are useful for both local and long distance shipping. The market use of this variety is the fresh eating market.

*Keeping quality.*—Good.

*Resistance to insects and disease.*—No susceptibilities were noted and was determined to be moderately resistant to bacterial leaf spot (*Xanthomonas campestris* pv. *pruni* (Smith) Dye) as is 'Flordaking' (not patented) in the field plots in College Station.

*Shipping quality.*—Average.

Although the new variety of peach tree possesses the described characteristics when grown under the ecological conditions prevailing in the central part of the San Joaquin Valley of California (near Fowler) or in south central Texas (near College Station and Yoakum), it will be understood that variations of the usual magnitude and characteristics incident to the changes in growing conditions, fertilization, pruning, and pest control are to be expected. It should also be realized by those skilled in the art that such equivalent constructions do not depart from the spirit and scope of the invention as set forth in the appended claim.

What is claimed is:

1. A new and distinct peach tree as described and illustrated herein.

* * * * *

TX2B6
2-22-01